(12) United States Patent  (10) Patent No.: US 6,607,491 B2
Sato  (45) Date of Patent: Aug. 19, 2003

(54) ULTRASONIC PROBE

(75) Inventor: Shohei Sato, Mitaka (JP)

(73) Assignee: Aloka Co., Ltd., Tokyo (JP)

( * ) Notice: Subject to any disclaimer, the term of this patent is extended or adjusted under 35 U.S.C. 154(b) by 0 days.

(21) Appl. No.: 10/104,845

(22) Filed: Mar. 22, 2002

(65) Prior Publication Data

US 2003/0060715 A1 Mar. 27, 2003

(30) Foreign Application Priority Data

Sep. 27, 2001 (JP) ........................................ 2001-298372

(51) Int. Cl.⁷ ............................ A61B 8/00; G03B 42/06; G11B 5/56
(52) U.S. Cl. ............................. 600/459; 367/7; 310/311
(58) Field of Search ................................. 600/459, 437, 600/443; 367/7; 73/589; 310/311, 313

(56) References Cited

U.S. PATENT DOCUMENTS 5,477,736 A   12/1995   Lorraine

FOREIGN PATENT DOCUMENTS

| JP | H3-275000 | | 12/1991 |
| JP | 11-123188 | * | 9/1997 |
| JP | 11-123188 | | 5/1999 |
| JP | 2001-45596 | | 2/2001 |

OTHER PUBLICATIONS

M.I. Haller and B.T. Khuri–Yakub. "Tapered Acoustic Matching Layers." 1993 Ultrasonics Symposium: pp. 505–508.

* cited by examiner

Primary Examiner—Marvin M. Lateef
Assistant Examiner—Ruby Jain
(74) Attorney, Agent, or Firm—Koda & Androlia

(57) ABSTRACT

An ultrasonic probe which is used for ultrasonic diagnosis comprises a transducer element, a sonic speed control element, and an acoustic matching layer. The sonic speed control element has a function to control the sonic speed of the ultrasonic waves traveling therethrough, and has an inclined characteristic in the sonic speed control effect in which the sonic speed control effect changes continuously along the direction of travel of the ultrasonic waves (thickness direction). The specific acoustic impedance of the sonic speed control element at the end near the living body corresponds to the specific acoustic impedance of the acoustic matching layer at the end away from the living body. The acoustic matching layer is preferably formed by layering 2 or 3 or more overlapped members. The boundary between two adjacent members has a shape with a plurality of hills and valleys. The crossing angle between the direction of travel of the ultrasonic waves and the boundary is set so that a predetermined condition is satisfied.

32 Claims, 11 Drawing Sheets

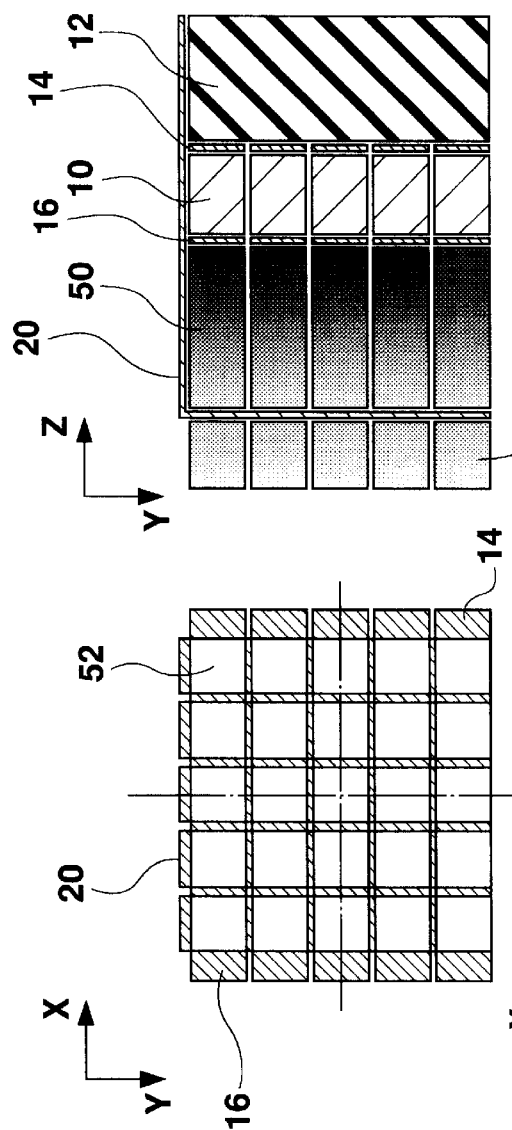
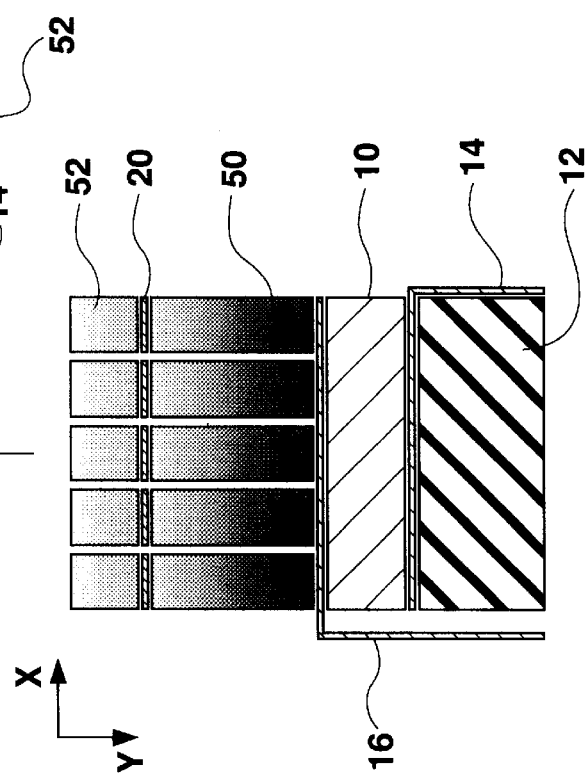
Fig. 5
Fig. 6
Fig. 7

ULTRASONIC PROBE

BACKGROUND OF THE INVENTION

1. Field of the Invention

The present invention relates to an ultrasonic probe and, more particularly, to an ultrasonic probe having a sonic speed control element.

2. Description of the Related Art

In ultrasonic diagnosis, in general, an ultrasonic probe is brought into contact with a surface of a living body and an ultrasonic wave is transmitted and/or received in that state. Japanese Patent Laid-Open Publication No. Hei 11-123188 discloses a new type of an ultrasonic probe which has a sonic speed control element. In this ultrasonic probe, a sonic speed control element is provided on the upper surface of a transducer for transmission/reception of ultrasonic waves. On the upper surface of the sonic speed control element, one or two acoustic matching layers are provided.

Similar to the transducer, a sonic speed control element is formed from, for example, a piezoelectric material. An external circuit is connected to the sonic speed control element. When the electrical impedance of the external circuit is varied, the ultrasonic propagation characteristic of the sonic speed control element is changed. In other words, mechanical or acoustic delay control which is different from the conventional electrical delay control can be realized through variations in the sonic speed of the ultrasonic waves traveling through the sonic speed control element.

Japanese Patent Laid-Open Publication No. Hei 11-123188 as described above also discloses more specifically another type of ultrasonic probe. The ultrasonic probe has a 1-D array transducer comprising a plurality of transducer elements. The arrangement direction (array direction) of the plurality of transducers is the electronic scan direction of the ultrasonic beams. A direction perpendicular to the arrangement direction is the elevation direction. In the ultrasonic probe, a plurality of sonic speed control elements which are arranged two-dimensionally is provided on the upper surface (surface near the living body) of the 1-D array transducer. More specifically, a plurality of sonic speed control elements are provided along the elevation direction for each one of the transducer elements. In this structure, for each transducer element, a signal lead is provided individually. A sonic speed control lead is provided individually for each plurality of sonic speed control elements (sonic speed control element column) arranged in the array direction. Further, a plurality of common ground leads are provided between the plurality of transducer elements and the plurality of sonic speed control elements. According to this structure, focus formation for ultrasonic beams, deflection of the ultrasonic beams, and scan of the ultrasonic beams can be realized both in the array direction and in the elevation direction. In other words, an advantage similar to a 2-D array transducer or a 1.5-D array transducer can be obtained. Moreover, there is an additional advantage that the number of signal lines can be significantly reduced compared to the conventional structures.

However, with the ultrasonic probe according to the above related art, because the specific acoustic impedances of the sonic speed control elements change dynamically, the specific acoustic impedance tends to not match at the boundary between a sonic speed control element and an acoustic matching layer, boundary between two adjacent acoustic matching layers, and boundary between an acoustic matching layer and the living body. When the specific acoustic impedance is not matched at these boundaries, unnecessary reflections of ultrasonic waves are generated at each of the boundaries and multiple reflections of the ultrasonic waves are generated between a plurality of boundaries. As a result, lingering (tailing) occurs in the transmitted ultrasonic waves and in the received ultrasonic waves, causing degradation in resolution in the distance direction. Also, the electrically formed focus and beam patterns are degraded. In summary, the mismatch of the specific acoustic impedance at each boundary causes degradation in the quality of ultrasonic images.

The above problem will now be described in more detail referring to FIG. 15, which shows the prior art. The schematic view shown in FIG. 15(B) shows a transducer including a transducer element 10 and a sonic speed control element 18. A backing layer 12 is provided at the lower side of the transducer element 10 (the side opposite the living body) with a signal lead 14 in between. A sonic speed control element 18 is provided at the upper side of the transducer element 10 (the side near the living body) with a common ground lead 16 in between. At the side of the sonic speed control element 18 near the living body, a first acoustic matching layer 22 and a second acoustic matching layer 24 are provided via a sonic speed control lead 20. The surface of the second acoustic matching layer 24 near the living body is brought into contact with the living body 26. As described above, the sonic speed control element 18 controls the sonic speed of ultrasonic waves traveling therethrough to realize acoustic delay.

As shown in FIG. 15(C), a transmitter-receiver 36 is connected between the signal lead 14 and the ground lead 16. An impedance controller 38 is connected between the sonic speed control lead 20 and the ground lead 16. The impedance controller 38 has a function such that the electrical impedance of the impedance controller can be varied. The impedance controller 38 and the sonic speed control element 18 form a closed circuit. When the electrical impedance of the impedance controller 38 is varied, the sonic speed of the ultrasonic waves traveling through the sonic speed control element 18 is changed.

FIG. 15(A) shows a graph indicating specific acoustic impedances at each position in the direction of travel of the ultrasonic waves. As shown in the figure, conventionally, the sonic speed control element 18 has a uniform specific acoustic impedance throughout the element. The specific acoustic impedance changes depending on the magnitude of the sonic speed variation. Reference numeral 32 shows a case of a maximum specific acoustic impedance and reference numeral 34 shows a case of a minimum specific acoustic impedance. Reference numeral 30 shows the variation width of the specific acoustic impedance.

The following problem is present in the related art shown in FIG. 15, as shown by reference numeral 28. The specific acoustic impedance of the end of the sonic speed control element 18 near the living body changes dynamically according to the sonic speed control. On the other hand, the specific acoustic impedances of the acoustic matching layers 22 and 24 do not dynamically change. Therefore, it is not always possible to match the specific acoustic impedance at the boundary between the sonic speed control element 18 and the acoustic matching layer 22. That is, a reflection wave which cannot be ignored is produced at this boundary. In addition, in the structure of FIG. 15, reflection waves are also produced at the boundaries between the acoustic matching layer 22 and the acoustic matching layer 24 and between the acoustic matching layer 24 and the living body 26, which also cannot be ignored. Therefore, in order to sufficiently take the advantage of the sonic speed control element, the reflection waves must be removed or reduced.

SUMMARY OF THE INVENTION

One object of the present invention is to improve the propagation characteristic of ultrasonic waves in an ultrasonic probe having a sonic speed control element.

Another object of the present invention is to enhance the quality of ultrasonic images.

Yet another object of the present invention is to provide an acoustic matching layer adapted for a sonic speed control element.

(1) In order to achieve at least one of the objects mentioned above, according to a first aspect of the present invention, there is provided an ultrasonic probe comprising a transducer element for transmitting and receiving ultrasonic waves; a sonic speed control element provided at the side of the transducer element near a living body and through which the ultrasonic waves transmitted or received by the transducer element travel, the sonic speed control element having a function to control the sonic speed of the ultrasonic waves traveling therethrough and having an inclined characteristic in the sonic speed control effect in which the sonic speed control effect is gradually changed along the direction of travel of the ultrasonic waves over the whole sonic speed control element or in a portion of the sonic speed control element in the direction of travel; and an acoustic matching layer provided at the side of the sonic speed control element near the living body.

According to the above structure, the inclined characteristic in the sonic speed control effect of the sonic speed control element can be used to solve or alleviate the problems of specific acoustic impedance mismatches as described above. For example, it is possible to set the sonic speed control effect in the sonic speed control element so that it is gradually decreased towards the living body, eventually to zero or a value close to zero at the end near the living body. In this case, the specific acoustic impedance at the end of the sonic speed control element near the living body is a constant value (or near a constant value with small variation) regardless of the sonic speed control operation. Thus, acoustic matching can more easily be achieved at the boundary between the end of the sonic speed control element near the living body and the acoustic matching layer.

The transducer is constructed from, for example, a piezoelectric material such as a PZT and a composite material. Similarly, the sonic speed control element is also constructed from, for example, a piezoelectric material such as a PZT and a composite material.

When the sonic speed control effect is varied in the above structure along the direction of travel of the ultrasonic waves (thickness direction), it is preferable that the variation be continuous, but a step-wise variation is also possible.

An electrode or a lead is provided as necessary between the transducer element and backing layer, between the transducer element and sonic speed control element, and between the sonic speed control element and acoustic matching layer. It is preferable that the thickness of these electronic elements be thin with respect to the wavelength $\lambda$ of the ultrasonic waves such that the thickness of these elements may be essentially ignored. With such a structure, the problem caused by the presence of these electronic elements, that is, mismatches in the specific acoustic impedance, can be prevented.

The present invention can be applied to various types of transducers such as a 1-D array transducer (used when a fixed focus is set in the elevation direction), a 1.5-D array transducer (used when variable focusing is executed in the elevation direction), and a 2-D array transducer (used in a case where beam scan is performed in two perpendicular directions). The present invention can be adapted for various electronic scan methods such as, for example, electronic linear scan and electronic sector scan.

According to another aspect of the present invention, it is preferable that the specific acoustic impedance characteristic within the acoustic matching layer is set based on the specific acoustic impedance of the sonic speed control element at the end near a living body and the specific acoustic impedance of the living body. With such a structure, unnecessary reflections of ultrasonic waves can be removed or reduced at the boundaries between the acoustic matching layer and sonic speed control element and between the acoustic matching layer and living body.

According to another aspect of the present invention, it is preferable for the sonic speed control effect of the sonic speed control element to be gradually reduced from the side of the sonic speed control element away from the living body towards the end of the sonic speed control element near the living body, and for the specific acoustic impedance of the acoustic matching layer to correspond to the specific acoustic impedance of the end of the sonic speed control element near the living body.

According to yet another aspect of the present invention, it is preferable that the sonic speed control element be made of a piezoelectric material, and that the piezoelectric constant of the piezoelectric material changes along the direction of travel. By varying the piezoelectric constant along the direction of travel of the ultrasonic waves (thickness direction), the sonic speed control effect (degree of sonic speed control) at each position in the direction of travel can be varied, and, at the same time, the amount of variation in the specific acoustic impedance at each position in the direction of travel can be manipulated.

When a sonic speed control element is manufactured, it is possible to employ a process, for example, in which, first, the entire piezoelectric material is polarized, then, thin electrode layers are formed on both surfaces of the piezoelectric material, and a cooling medium is contacted to a first surface of the piezoelectric material and a heating medium is contacted to a second surface of the piezoelectric material for partial polarization vanishing process. In this case, an inclined characteristic in the polarizability can be obtained in which the polarizability continuously varies from a value of zero near the second surface towards the first surface. In other words, the portion of the piezoelectric material near the second surface has a piezoelectric constant of approximately zero, and a gradient in the piezoelectric constant is created from this portion towards the first surface.

According to another aspect of the present invention, it is preferable that the piezoelectric constant at the end of the sonic speed control element near the living body is zero. In other words, at the end of the sonic speed control element near the living body, the sonic speed does not change regardless of the sonic speed control, and the specific acoustic impedance also does not vary. Because of this, by coinciding the specific acoustic impedance of the acoustic matching layer with that of the end of the sonic speed control element near the living body, the specific acoustic impedance can always be matched at the boundary between the acoustic matching layer and the sonic speed control element regardless of the sonic speed control.

According to another aspect of the present invention, it is preferable that the piezoelectric constant gradually decreases from the middle portion of the sonic speed control element towards the end of the sonic speed control element near the living body. It is also possible to vary the piezoelectric constant entirely along the direction of travel of the ultrasonic waves, but in order to match the specific acoustic impedance at the boundary between the acoustic matching layer and the sonic speed control element, it is sufficient to partially reduce the piezoelectric constant. Further, instead of varying the piezoelectric constant, it is also possible to mix a high dielectric constant, non-piezoelectric material into the sonic speed control element, with the amount of mixing varied along the thickness direction of the sonic speed control element.

According to another aspect of the present invention, it is preferable that the piezoelectric constant gradually decreases from the middle portion of the sonic speed control element towards the end of the sonic speed control element near the living body and towards the end of the sonic speed control element away from the living body. According to a further aspect of the present invention, it is preferable that the piezoelectric constants at the ends of the sonic speed control element near the living body and away from the living body are zero.

According to another aspect of the present invention, it is preferable that the acoustic matching layer has an inclined characteristic in the specific acoustic impedance in which the specific acoustic impedance gradually changes from the end away from the living body toward the end near the living body. In this manner, by also providing an inclined characteristic in the specific acoustic impedance for the acoustic matching layer, unnecessary reflection of ultrasonic waves can be further reduced and the quality of the ultrasonic images can be improved.

According to another aspect of the present invention, it is preferable that the specific acoustic impedance of the end of the acoustic matching layer away from the living body matches with the specific acoustic impedance of the end of the sonic speed control element near the living body; and the specific acoustic impedance of the end of the acoustic matching layer near the living body matches with the specific acoustic impedance of the living body.

According to another aspect of the present invention, it is preferable that the acoustic matching layer comprises a first member and second member having different specific acoustic impedances from each other; and that the compositional ratio between the first member and the second member changes along the direction of travel. Here the compositional ratio refers to the ratio of presence per unit volume.

According to yet another aspect of the present invention, it is preferable that the first member has a specific acoustic impedance which is equal to the specific acoustic impedance of the end of the sonic speed control element near the living body, and that the second member has a specific acoustic impedance which is equal to the specific acoustic impedance of the living body. The first member can be formed from, for example, a material similar to the sonic speed control element (but a non-polarized material). The second member can be, for example, a composite material in which an additive such as silica is added to a base material such as liquid phase silicone. In this case, the specific acoustic impedance of the second member can be adjusted by adjusting the amount of the added additive.

According to another aspect of the present invention, it is preferable that the first member comprises a plurality of pyramid elements having a pinnacle shape projecting towards the living body; and that the second member is filled into the gap between the plurality of pyramid elements. The pyramid element may be a quadrangular pyramid or hexagonal pyramid. It is preferable that the arrangement pitch of the plurality of pyramid elements be sufficiently small compared to the wavelength $\lambda$ of the ultrasonic waves, and can be, for example, less than or equal to $\lambda/5$. The plurality of pyramid elements can be formed through various methods such as, for example, cutting, pressing, or etching applied on a plate-shaped first member.

Furthermore, the sonic speed control elements can have a similar structure. That is, it is possible to form a plurality of pyramid elements from a piezoelectric material and fill a non-piezoelectric material having a high dielectric constant into the gaps.

(2) In order to achieve at least one of the objects mentioned above, according to the present invention, there is provided an ultrasonic probe comprising N transducer elements for transmitting and receiving ultrasonic waves; N×M sonic speed control elements provided at the ends of the N transducer elements near the living body and through which the ultrasonic waves travel, with M sonic speed control elements provided for each transducer element, each sonic speed control element having a function to control the sonic speed of the ultrasonic waves traveling therethrough and having an inclined characteristic in the sonic speed control effect in which the sonic speed control effect gradually changes along the direction of travel of the ultrasonic waves over the whole sonic speed control element or in a portion of the sonic speed control element in the direction of travel; and N×M acoustic matching layers provided at the side of the N×M sonic speed control elements near the living body.

(3) In order to achieve at least one of the objects mentioned above, according to the present invention, there is provided an ultrasonic probe comprising a transducer element for transmitting and receiving ultrasonic waves; a sonic speed control element provided at the side of the transducer element near the living body and through which the ultrasonic waves travel, the sonic speed control element having a function to control the sonic speed of the ultrasonic waves traveling therethrough; and an acoustic matching layer provided at the side of the sonic speed control element near the living body and having an inclined characteristic in the specific acoustic impedance in which the specific acoustic impedance monotonically changes along the direction of travel of the ultrasonic waves.

According to another aspect of the present invention, it is preferable that the sonic speed control element has a non-inclined characteristic in the sonic speed control effect in which the sonic speed control effect is uniform at every position in the direction of travel. Even if the sonic speed control element has a non-inclined characteristic (that is, uniform characteristic) in the specific acoustic impedance, by providing, corresponding to the sonic speed control element, an acoustic matching layer in which the specific acoustic impedance monotonically varies, unnecessary reflections of ultrasonic waves can be reduced and the sonic speed control element can function satisfactorily.

According to another aspect of the present invention, it is preferable that the sonic speed control element has an inclined characteristic in the sonic speed control effect in which the sonic speed control effect gradually changes along the direction of travel. With such a structure, the propagation efficiency of the ultrasonic waves can be improved by the inclined characteristic in the sonic speed control effect of the sonic speed control element and the inclined characteristic in the specific acoustic impedance of the acoustic matching layer.

According to another aspect of the present invention, it is preferable that the acoustic matching layer comprises a first member and a second member overlapped in the direction of travel; the first member and the second member have different specific acoustic impedances from each other; and the boundary between the first member and the second member has a shape with a plurality of hills and valleys.

According to another aspect of the present invention, it is preferable that when the crossing angle between the direction of travel and the boundary is $\theta$, the sonic speed of the ultrasonic waves within the first member is $C_1$, and the sonic speed of the ultrasonic waves within the second member is $C_2$, a condition, $$C_2 < C_1 < C_2/\cos \theta \quad \text{(Equation 1)}$$

or a condition, $$C_2 = C_1 \quad \text{(Equation 2)}$$

is satisfied.

When the above equation (2) is satisfied, that is, when the sonic speeds in two members (two sub-layers) forming the acoustic matching layer are equal, no refraction or total internal reflection is produced at the boundary between the two members in accordance with Snell's law.

On the other hand, when the above equation (2) is not satisfied, that is, when the sonic speeds differ in the two members forming the acoustic matching layer, the following is true. Here, a "first member" is defined as the member in which the sonic speed is larger among the two members forming the acoustic matching layer and a "second member" is defined as the member in which the sonic speed is smaller.

Under the above condition, $C_2 < C_1$, when an ultrasonic wave is incident from the first member into the second member, no total internal reflection of the ultrasonic wave is generated regardless of the size of $\theta$, in accordance to Snell's law. In contrast, when an ultrasonic wave is incident from the second member, in which the sonic speed is smaller, to the first member, in which the sonic speed is larger, whether or not a total internal reflection is generated at the boundary depends on the incident angle of the ultrasonic wave with respect to the boundary. Here, the direction of the actual propagation of the ultrasonic waves is primarily in the direction of normal with respect to the surface of the acoustic matching layer (thickness direction). The direction is already defined as the direction of travel. A condition in equation (1), $C_1 < C_2/\cos \theta$, is for preventing the total internal reflection when ultrasonic waves are incident from the second member into the first member along the direction of normal. The slope of each of the sections (each surface elements) is determined to satisfy equation (1).

More specifically, the hills-and-valleys surface shape of the boundary and the sonic speeds in the first and second members are determined to satisfy the equations (1) or (2). In this manner, the generation of total internal reflection can be prevented or inhibited for both cases of transmission and reception of ultrasonic waves.

In addition, it is possible to design the acoustic matching layer so that the transmitted ultrasonic waves are incident from the first member into the second member, or, alternatively, from the second member into the first member.

According to another aspect of the present invention, it is preferable that one member, of the first member and the second member, provided near the living body has a specific acoustic impedance corresponding to the specific acoustic impedance of the living body; and the other member of the first member and the second member provided away from the living body has a specific acoustic impedance corresponding to the specific acoustic impedance of the sonic speed control element.

According to a further aspect of the present invention, it is preferable that one member of the first member and the second member comprises a plurality of first elements having a pinnacle shape; and the other member of the first member and the second member comprises a plurality of second elements having a shape to fit in the valley section between the plurality of first elements.

According to yet another aspect of the present invention, it is preferable that the pinnacle shape is a shape with a triangular vertical cross section and a quadrangle horizontal cross section, a pyramid shape, or the like.

According to another aspect of the present invention, it is preferable that the arrangement pitch of the plurality of first elements is less than or equal to ½ of the wavelength of the ultrasonic waves. According to another aspect of the present invention, it is preferable that the depth of the valley section is greater than or equal to ½ of the wavelength of the ultrasonic waves.

(4) In order to achieve at least one of the objects mentioned above, according to the present invention, there is provided an ultrasonic probe, comprising a transducer element for transmitting and receiving ultrasonic waves; a sonic speed control element provided at the side of the transducer element near the living body and through which the ultrasonic waves travel, the sonic speed control element having a function to control the sonic speed of the ultrasonic waves traveling therethrough; and an acoustic matching layer provided at the side of the sonic speed control element near the living body and having an inclined characteristic in the specific acoustic impedance in which the specific acoustic impedance monotonically changes along the direction of travel, the acoustic matching layer made of n members (where n is an integer greater than or equal to 3) overlapped in the direction of travel, and the specific acoustic impedances of the n members changing in steps along the direction of travel.

According to another aspect of the present invention, it is preferable that each of the boundaries between the n members has a shape with hills and valleys.

According to another aspect of the present invention, it is preferable that when the crossing angle between the direction of travel and the boundary between the k-th member (where k is an integer satisfying the condition, $1 \leq k \leq (n-1)$) and (k+1)-th member is $\theta_k$, the sonic speed of the ultrasonic waves within the k-th member is $C_k$, and the sonic speed of the ultrasonic waves within the (k+1)-th member is $C_{k+1}$, a condition, $$C_{k+1} < C_k < C_{k+1}/\cos \theta_k$$

or a condition, $$C_{k+1} = C_k$$

is satisfied.

With such a structure, in an acoustic matching layer comprising three or more members (sub-layers), the specific acoustic impedance can substantially be continuously varied along the direction of travel of the ultrasonic waves. That is, an inclined characteristic in the specific acoustic impedance can be provided for the acoustic matching layer. Thus, total internal reflection produced at the boundary can be inhibited and the proper function of the sonic speed control element can be sufficiently achieved.

According to another aspect of the present invention, it is preferable that the member, among the n members, that is closest to the living body has a specific acoustic impedance corresponding to the specific acoustic impedance of the living body; and the member, among the n sub-layers, that is closest to the sonic speed control element has a specific acoustic impedance corresponding to the specific acoustic impedance of the sonic speed control element.

According to another aspect of the present invention, it is preferable that one member of the k-th member and the (k+1)-th member comprises a plurality of first elements having a pinnacle shape; and the other member of the k-th member and the (k+1)-th member comprises a plurality of second elements having a shape that fits into the valley section between the plurality of first elements.

According to another aspect of the present invention, it is preferable that the pinnacle shape is a pyramid. According to another aspect of the present invention, it is preferable that the arrangement pitch of the plurality of first elements is less than or equal to ½ of the wavelength of the ultrasonic waves. According to another aspect of the present invention, it is preferable that the depth of the valley section at the plurality of hills and valleys is greater than or equal to ½ of the wavelength of the ultrasonic waves.

BRIEF DESCRIPTION OF THE DRAWING(s)

FIG. 5 is a top view of a ultrasonic probe according to the present invention.

FIG. 6 is a first cross sectional view of the ultrasonic probe according to the present invention.

FIG. 7 is a second cross sectional view of the ultrasonic probe according to the present invention.

DESCRIPTION OF PREFERRED EMBODIMENTS

The preferred embodiments of the present invention will now be described with reference to the drawings.

Figure 1:
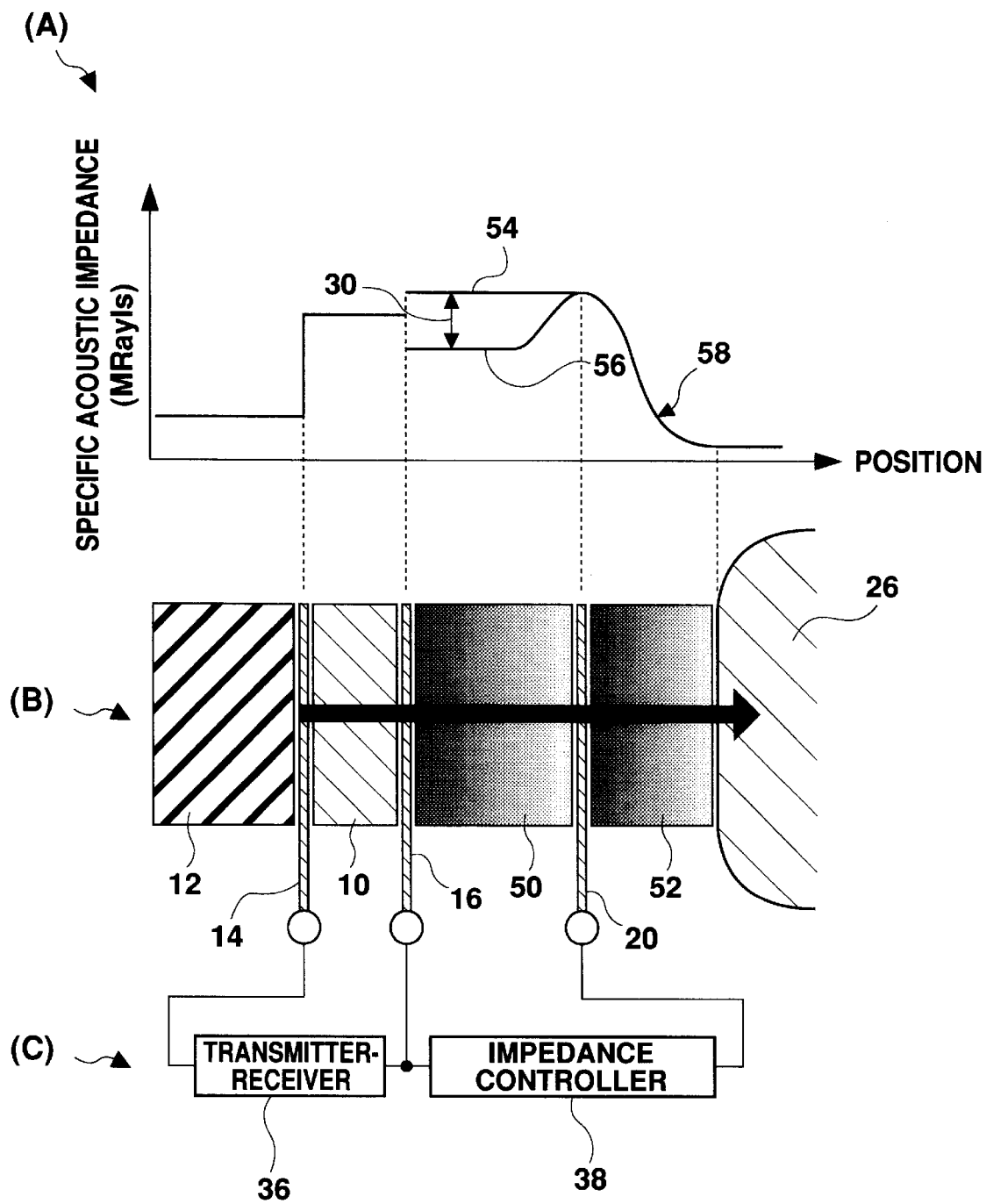
FIG. 1 is a drawing for explaining the principle of an ultrasonic probe according to the present invention.

FIG. 1 shows the principle of an ultrasonic probe according to the present invention. An ultrasonic probe in this embodiment comprises an array transducer as shown in FIG. 7. FIG. 1 shows one of the transducer elements 10 of the array transducer along with other structures. FIG. 1(B) is a cross sectional view of a portion of the ultrasonic probe, FIG. 1(A) shows the variation in the specific acoustic impedance along the direction of travel of the ultrasonic waves (thickness direction), and FIG. 1(C) shows a plurality of electrical circuits.

As shown in FIG. 1(B), the transducer element 10 is for transmitting/receiving ultrasonic waves. The transducer element 10 is made of, for example, a PZT or composite piezoelectric material. At the side of the transducer element 10 away from the living body, a backing layer 12 is abutted with a signal lead 14 in between. The backing layer 12 is a known member for absorbing unnecessary ultrasonic waves radiated from the transducer element 10 to the rear side.

At the side of the transducer element 10 near the living body, a sonic speed control element 50 is abutted with a ground lead 16 in between. As described above, the sonic speed control element 50 is a member for controlling the sonic speed of the ultrasonic waves traveling therethrough. An impedance controller 38, which will be described below, is connected to the sonic speed control element 50, and the sonic speed control element 50 and the impedance controller 38 form a closed circuit. When the internal electrical impedance of the impedance controller 38 is varied, the acoustic characteristic of the sonic speed control element 50 is also varied. That is, the sonic speed of the ultrasonic waves traveling therethrough is changed. In this manner, the ultrasonic waves can be acoustically delayed. This sonic speed control element 50 is disclosed in Japanese Patent Laid-Open Publication No. Hei 11-123188. In this embodiment, the sonic speed control element 50 is made of a material similar to that for the transducer element 10, for example, a PZT or composite piezoelectric material.

When the degree of the sonic speed control (amount of delay) of the sonic speed control element 50 is varied, the specific acoustic impedance of the sonic speed control element 50 is changed. In the sonic speed control element 50 of this embodiment, the piezoelectric constant is set to gradually decrease from the center portion (middle portion) to the end near the living body. As a result, the sonic speed control function in the sonic speed control element 50 decreases from the center portion towards the end near the living body. The piezoelectric constant at the end near the living body is substantially zero. Therefore, even when the sonic speed control is performed, the specific acoustic impedance at the end near the living body is always maintained at a constant value. In other words, as indicated by reference numerals 54, 56 and 30, the specific acoustic impedance is significantly varied in the vertical direction at the region from the end away from the living body to the center portion of the sonic speed control element 50 depending on the magnitude of the degree of sonic speed control, but in the region from the center portion to the end near the living body, the variation in the specific acoustic impedance decreases as the distance to the living body decreases (to a constant specific acoustic impedance value at the portion closest to the living body) This is because the piezoelectric constant is continuously reduced from the center portion towards the end near the living body, as described above. Because the specific acoustic impedance at the end of the sonic speed control element 50 near the living body is always constant, by setting the specific acoustic impedance at the end of the sonic speed control element 50 near the living body substantially equal to the specific acoustic impedance of the acoustic matching layer 52, a step in the specific acoustic impedance at the boundary between the sonic speed control element 50 and the acoustic matching layer 52 can always be prevented. In other words, the reflections of ultrasonic waves produced at the boundary can be. efficiently inhibited regardless of the operational state of the sonic speed control element 50.

Even if the sonic speed control element 50 and the transducer element 10 are made of the same material, in the structure of FIG. 1, because the specific acoustic impedance at the end of the sonic speed control element 50 away from the living body changes, it is not possible to completely prevent the reflection of the ultrasonic waves at the boundary between the sonic speed control element 50 and the transducer element 10. To this end, it is possible to continuously decrease the piezoelectric constant from the center portion of the sonic speed control element 50 to the end away from the living body. In this case, the piezoelectric constant at the end away from the living body may be set at zero.

In this embodiment, the piezoelectric constant is varied continuously in the sonic speed control element 50 from the center portion towards the end near the living body, in the thickness direction, but it is also possible to continuously vary the piezoelectric constant over the entire sonic speed control element 50 in the thickness direction, that is, from the end away from the living body to the end near the living body. Further, it is also possible to step-wise vary the piezoelectric constant instead of continuous variation.

As shown in FIG. 1(B), an acoustic matching layer 52 is provided at the side of the sonic speed control element 50 near the living body with a sonic speed control lead 20 in between. The acoustic matching layer 52 is a member for matching the specific acoustic impedance between the sonic speed control element 50 and the living body 26. In the embodiment, the acoustic matching layer 52 has an inclined characteristic in the specific acoustic impedance in which the specific acoustic impedance is continuously changed along the thickness direction. More specifically, the specific acoustic impedance of the acoustic matching layer 52 at the end away from the living body is substantially equal to the specific acoustic impedance of the sonic speed control element 50 at the end near the living body and the specific acoustic impedance of the acoustic matching layer 52 at the end near the living body is substantially equal to the specific acoustic impedance of the living body 26. Therefore, because both the sonic speed control element 50 and the acoustic matching layer 52 have an inclined characteristic in the specific acoustic impedance, it is possible to efficiently propagate the ultrasonic waves transmitted from the transducer element 10 to the living body 26, with as much removal as possible of unnecessary internal reflections. Similarly, it is possible to efficiently propagate the ultrasonic waves coming back from the living body 26 to the transducer element 10 with as much removal as possible of unnecessary internal reflections. Thus, it is possible to solve the problem of waveform collapse of the ultrasonic waves or the like, and thereby, improve the quality of ultrasonic images.

The ground lead 16 and the sonic speed control lead 20 are constructed from, for example, a metal such as copper. Thus, theoretically, a large step is present in the specific acoustic impedance at the lead. However, by thinning the lead so that the thickness of the lead can be substantially ignored compared to the wavelength of the ultrasonic waves, in practice, the step in the specific acoustic impedance does not pose any significant problem.

In the structure shown in FIG. 1, only one acoustic matching layer is used. It is also possible to use two overlapped acoustic matching layers and set one or both layers to have the above inclined characteristic in the specific acoustic impedance. Also, in FIG. 1, no acoustic lens is provided, but it is possible, as necessary, to provide an acoustic lens at the side of the acoustic matching layer 52 near the living body.

Thin electrode layers which is not shown are formed respectively on one surface and the other surface of the transducer element 10. The signal lead 14 and ground lead 16 are respectively connected to the electrode layers. A transmitter-receiver 36 is connected between the leads 14 and 16. Transmission signals are supplied from the transmitter-receiver 36 to the transducer element 10. Similarly, the received signal produced when an ultrasonic wave is received at the piezoelectric element 10 is output to the transmitter-receiver 36.

Similar to the transducer element 10 as described above, thin electrode layers are formed respectively on one surface and the other surface of the sonic speed control element 50. The ground lead 16 and sonic speed control lead 20 are respectively connected to the electrode layers. An impedance controller 38 is connected between the leads 16 and 20. As described above, the impedance controller 38 controls the acoustic characteristic of the sonic speed control element 50 by varying the electrical impedance of the impedance controller 38. More specifically, a variation of the electrical impedance of the impedance controller 38 causes variation in the amount of sonic speed control in the sonic speed control element 50.

In the embodiment, as shown in FIG. 1(B), the ground lead 16 functions as the common ground, thereby, allowing reduction in the number of signal lines extending outside.

Figure 2:
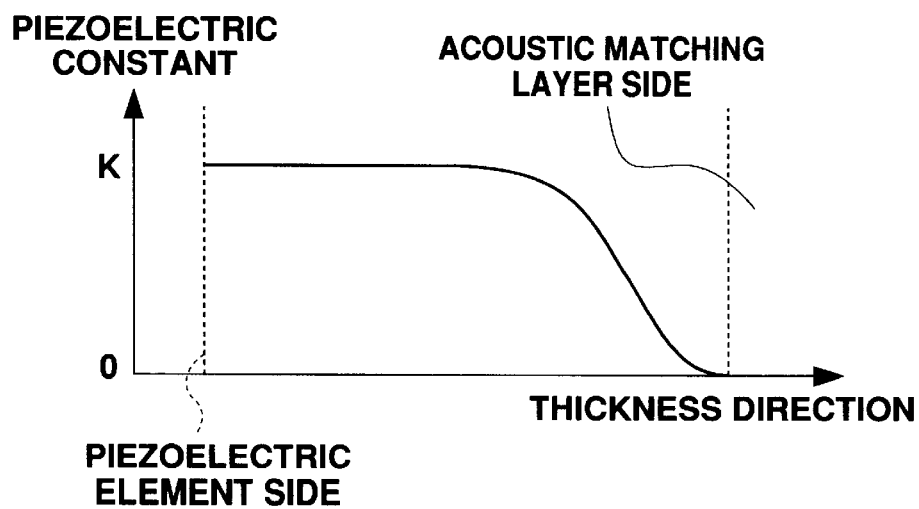
FIG. 2 is a figure showing variation in piezoelectric constant in the thickness direction of the sonic speed control element shown in FIG. 1.

FIG. 2 is a graph showing variation in the piezoelectric constant along the thickness direction of the sonic speed control element 50. The piezoelectric constant at the end near the transducer element, that is, the end away from the living body, is a predetermined value K. In the thickness direction, the piezoelectric constant gradually decreases from the center portion towards the end near the acoustic matching layer 52, that is, the end near the living body, ultimately to zero at the end surface near the living body. A method for setting such inclined characteristic in piezoelectric constant will be described later referring to FIGS. 8 and 9.

Figures 3, 4:
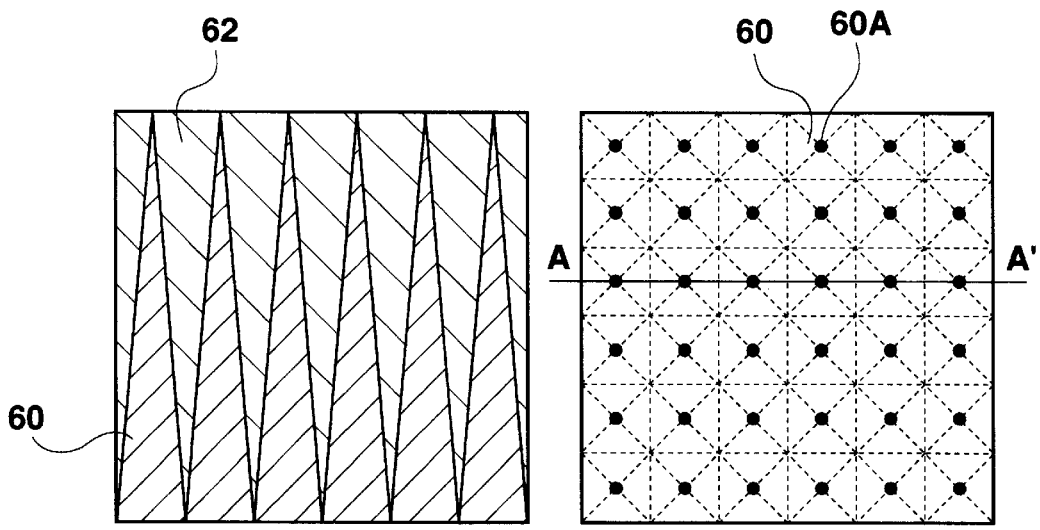
FIG. 3 is a cross sectional view of the acoustic matching layer shown in FIG. 1.
FIG. 4 is a top view of the acoustic matching layer shown in FIG. 1.

FIGS. 3 and 4 show an example of the acoustic matching layer 52 shown in FIG. 1. FIG. 3 is a vertical cross section of the acoustic matching layer and FIG. 4 is a view of the acoustic matching layer seen from the living body. The position of the cross sectional view of FIG. 3 is indicated by the A–A' line in FIG. 4. In the embodiment, the acoustic matching layer 52 is constructed from two members. More specifically, the acoustic matching layer 52 is constructed from a first member 60 and a second member 62.

The first member 60 comprises a plurality of pyramid shaped elements having its vertex 60A directed towards the living body. The pyramid shaped element is, for example, a pyramid having a quadrangle base. The second member 62 fills the gap. In this structure, one or a plurality of materials for the first member 60 is selected such that the specific acoustic impedance of the fist member 60 is equivalent to that of the sonic speed control element 50 at the end near the living body. In contrast, one or a plurality of materials for the second member 62 is selected such that the specific acoustic impedance of the second member 62 is equivalent to that of the living body. With such a structure, the end of the acoustic matching layer 52 away from the living body and the end of the sonic speed control element 50 near the living body are acoustically matched. At the same time, the end of the acoustic matching layer 52 near the living body and the living body are acoustically matched. Here, the first member 60 can be constructed from, for example, a PZT or a composite material, similar to the sonic speed control element 50. The second member 62 can be constructed by mixing an additive such as silica powder, titanium oxide, etc., to a base material such as polyurethane, silicon rubber, etc. In this case, a desired specific acoustic impedance can be realized by adjusting the amount of additive to be added.

In order to manufacture an acoustic matching layer shown in FIGS. 3 and 4, a plurality of V-shaped channels extending in the X direction and a plurality of V-shaped channels extending in the Y direction are formed on a first material having a plate-like shape. The V-shaped channel may be formed by first tilting the first material with respect to a dicing saw, cutting the fist material in that state to form one inclined surface, tilting the first material in the other direction with respect to the dicing saw, and cutting the first material to form the other inclined surface. After a plurality of pyramid-shaped elements are formed through such a machining process, the second material in the liquid phase is poured into the gaps. The first material onto which the second material is poured is then left in vacuum to remove bubbles in the second material. The structure is then naturally left under normal temperature, normal humidity, and normal pressure, to cure the second material. Alternatively, any other formation method can be used for forming the plurality of pyramid-shaped elements, in place of the cutting process. The arrangement pitch of the plurality of pyramid-shaped elements is preferable as small as possible compared to the wavelength ($\lambda$) of the ultrasonic waves, and can be, for example, about $\lambda/5$.

FIGS. 5, 6, and 7 show an ultrasonic probe according to the embodiment. FIG. 5 is a top view, FIG. 6 is a first cross sectional view, and FIG. 7 is a second cross sectional view, respectively of an ultrasonic probe.

The ultrasonic probe comprises a plurality of transducer elements 10 arranged in the Y direction (electronic scan direction), a plurality of sonic speed control elements 50 which are two-dimensionally arranged, a plurality of acoustic matching layers 52 which are two-dimensionally arranged, and a backing layer 12. Each transducer element 10 has a plate-like shape extending in the elevation direction (X direction). Here, a signal lead 14 is provided for each transducer element 10 between each of the transducer elements 10 and the backing layer 12. Further, a ground lead 16 is provided for each transducer element 10 between each of the transducer elements 10 and each of the sonic speed control elements 50. The signal leads 14 and the ground leads 16 extend in the X direction. The plurality of signal leads 14 are aligned in the Y direction and the plurality of ground leads 16 are also aligned in the Y direction.

For each piezoelectric element 10, a plurality of sonic speed control elements 50 is provided along the X direction. For each of the sonic speed control elements 50, an acoustic matching layer 52 is provided. A plurality of sonic speed control leads 20 is provided between the plurality of sonic speed control elements 50 and the plurality of acoustic matching layers 52. More specifically, a sonic speed control lead 20 is provided for a column formed from a plurality of sonic speed control elements 50 aligned in the Y direction.

In the above structure, a gap for preventing propagation of ultrasonic waves is present respectively between each of the plurality of transducer elements 10, between each of the plurality of sonic speed control elements 50, and between each of the plurality of acoustic matching layers 52. In other words, cross-talk is prevented by these gaps. It is also possible to inject a filler which functions as an acoustic shield into these gaps.

Both the sonic speed control elements 50 and the acoustic matching layers 52 have the inclined characteristic in the specific acoustic impedance as described referring to FIG. 1. Because of this, it is possible to inhibit unnecessary reflections of the ultrasonic waves within the ultrasonic probe and improve the propagation efficiency of the ultrasonic waves.

In the embodiment shown in FIGS. 5, 6, and 7, N piezoelectric elements 10 are provided along the Y direction. Also, M sonic speed control elements 50 are provided for each transducer element 10. In other words, a total of N×M sonic speed control elements 50 and corresponding N×M acoustic matching layers 52 are provided. With such a structure, ultrasonic beams can be scanned along the Y direction, that is, the array direction, and, at the same time, along the X direction. In a conventional 2-D array transducer, for example, N×M signal lines are necessary, but in the ultrasonic probe of the embodiment, for example, only N signal lines are necessary.

Figure 8:
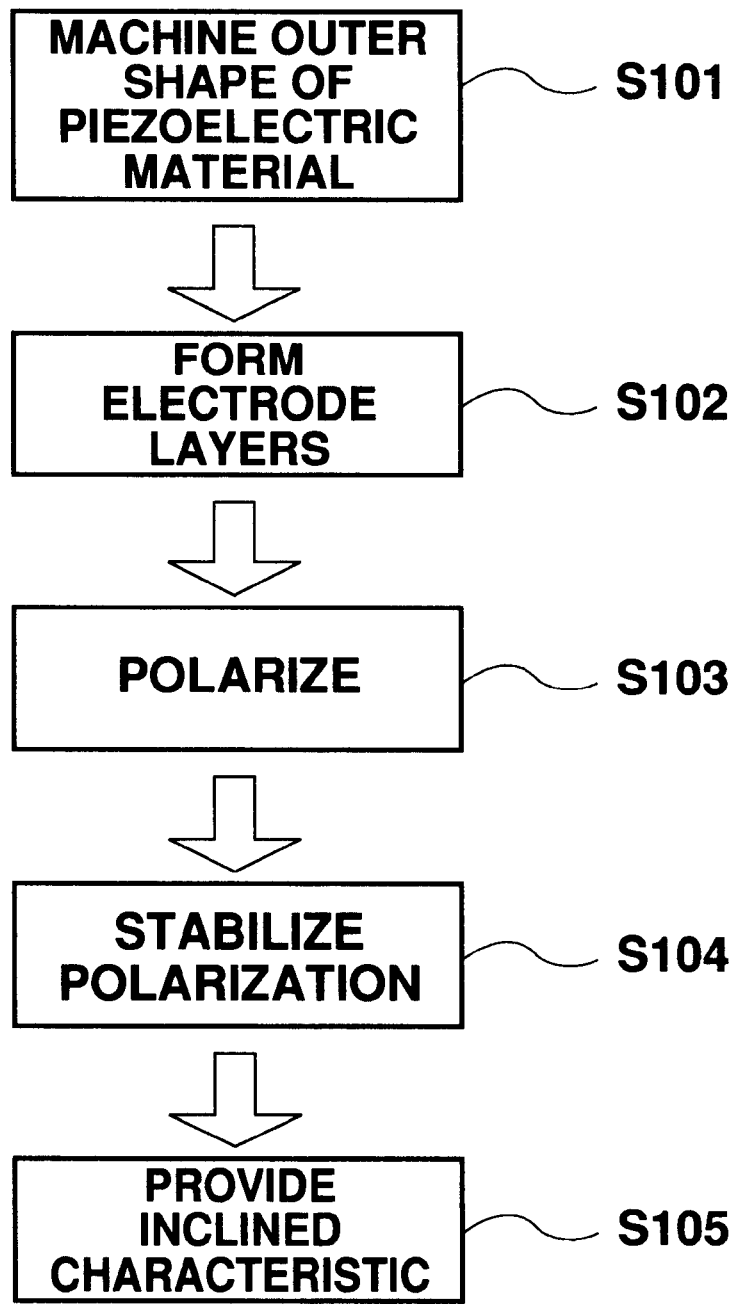
FIG. 8 is a flowchart showing an example method for manufacturing a sonic speed control element according to the present invention.

FIG. 8 is a flowchart showing a method for manufacturing a sonic speed control element 50 shown in FIG. 1. First, at step S101, a piezoelectric plate is prepared and machined into a predetermined size. Then, a lapping process is applied to one surface and the other surface of the piezoelectric plate in order to improve the flatness of each surface of the piezoelectric plate and thereby secure thickness precision.

Next, at step S102, an electrode layer is formed respectively on one surface and the other surface of the piezoelectric plate. In this case, a nickel chrome layer having a thickness of approximately 0.1 $\mu$m is formed as a base layer on each surface through sputtering or the like. The n, a metal layer having a thickness of approximately 0.5 $\mu$m is formed on the nickel chrome layer through sputtering.

At step S103, polarization process is applied. More specifically, a direct current high voltage is applied to the piezoelectric plate. When a PZT or the like which has a low Curie temperature of, for example, 150° C. is used as a material forming the piezoelectric plate, a direct current voltage of about 1500 V is applied per 1 mm of thickness. The application time is, for example, about 5 minutes. Then, in order to stabilize the polarization state in the piezoelectric plate, the piezoelectric plate is left, for example, for 3 days under normal temperature, normal humidity, and normal pressure (step S104).

Figure 9:
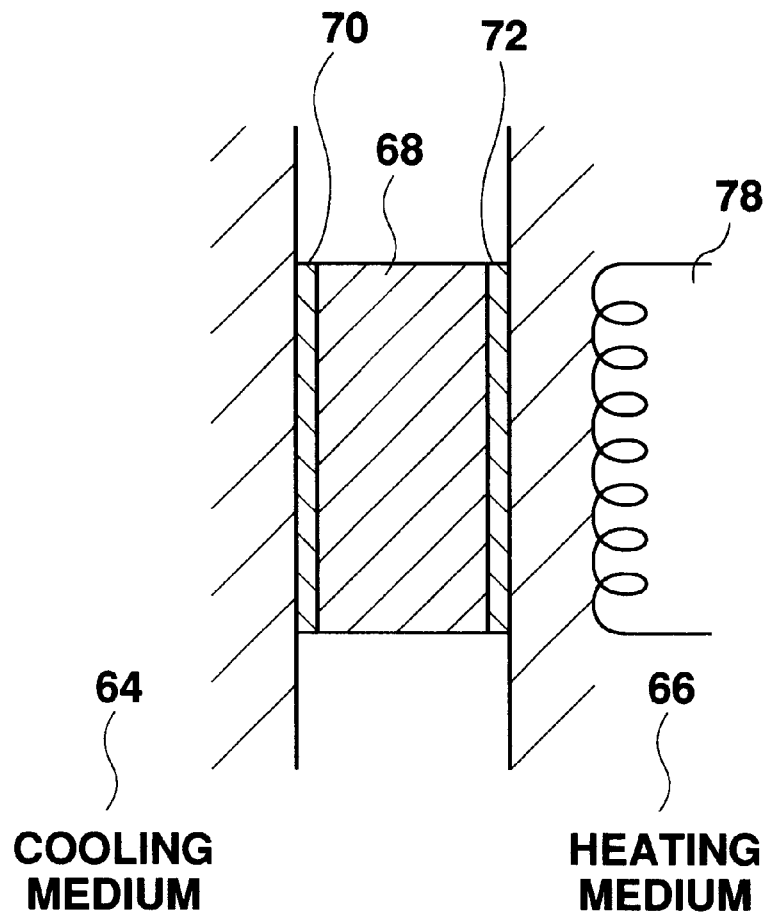
FIG. 9 is a drawing for explaining a partial polarization vanishing process for a piezoelectric material.

Then, at step S105, a special treatment is applied for forming the inclined characteristic in the piezoelectric constant as described above. More specifically, as shown in FIG. 9, a cooling medium 64 is contacted to the electrode layer 70 formed on one surface of the piezoelectric plate 68. On the other hand, a heating medium 66 is contacted to the electrode layer 72 formed on the other surface of the piezoelectric plate 68. In this state, both heating and cooling processes are simultaneously applied. As the cooling medium 64, a copperplate material having cooling water circulating inside can be used. As a heating medium 66, a copperplate material having a built-in heater can be used. The heating temperature is set above the Curie temperature of the material forming the piezoelectric plate. The slope of the polarizability can be controlled by the heating duration and temperature. The polarity to which the inclined characteristic is to be added can be either the positive polarity or the negative polarity. According to this method, the polarization at the end of the piezoelectric plate 68 near the heating medium can be to disappear without eliminating the polarization at the end of the piezoelectric plate 68 near the cooling medium. That is, through such process, it is possible to gradually decrease the piezoelectric constant from positions near the cooling medium toward the heating medium, to eventually a piezoelectric constant of zero at the end near the heating medium. In other words, a sonic speed control element having the inclined characteristic in the piezoelectric constant can be manufactured.

As an alternative, after the above process, the orientation of the piezoelectric plate 68 can be inverted to allow contact of the cooling medium 64 with the electrode layer 72 and contact of the heating medium 66 with the electrode layer 70, and the heating and cooling processes similar to the above can be applied. In this manner, a sonic speed control element having a mountain-shaped or bell-shaped inclined characteristic in the piezoelectric constant can be manufactured in which the piezoelectric constant is gradually decreased from the center portion toward both ends, to eventually a value of zero at the ends.

After step S105 is completed, vertical and horizontal cutting processes are performed on the piezoelectric body (sonic speed control element) 68 as necessary. Other components are combined to the processed piezoelectric body. Ultimately, an ultrasonic probe as shown in FIGS. 5, 6, and 7 is constructed.

In the above embodiment, a partial polarization elimination process is applied after the polarization process. It is also possible to obtain the above inclined characteristic in the piezoelectric constant by, for example, mixing a non-piezoelectric material having a high dielectric constant into the piezoelectric material with the mixing ratio continuously varied along the thickness direction.

Referring to FIGS. 10 through 14, the conditions for allowing the acoustic matching layer having the inclined characteristic in the piezoelectric constant to effectively function will now be discussed.

Figure 10:
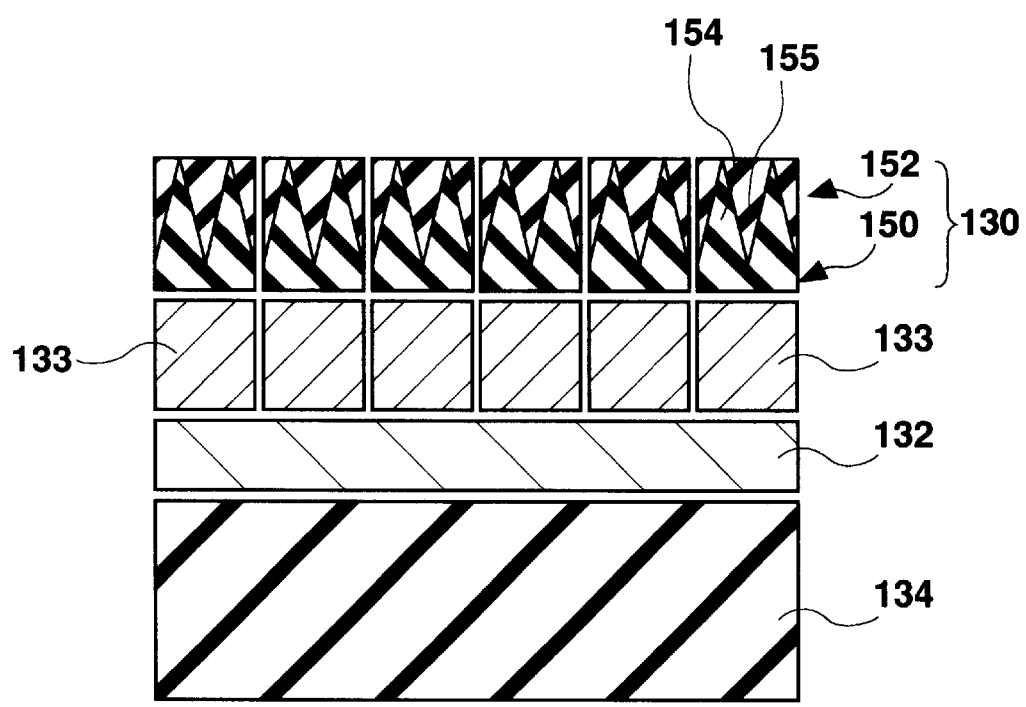
FIG. 10 is a cross sectional view of another ultrasonic probe according to the present invention.
Figure 11:
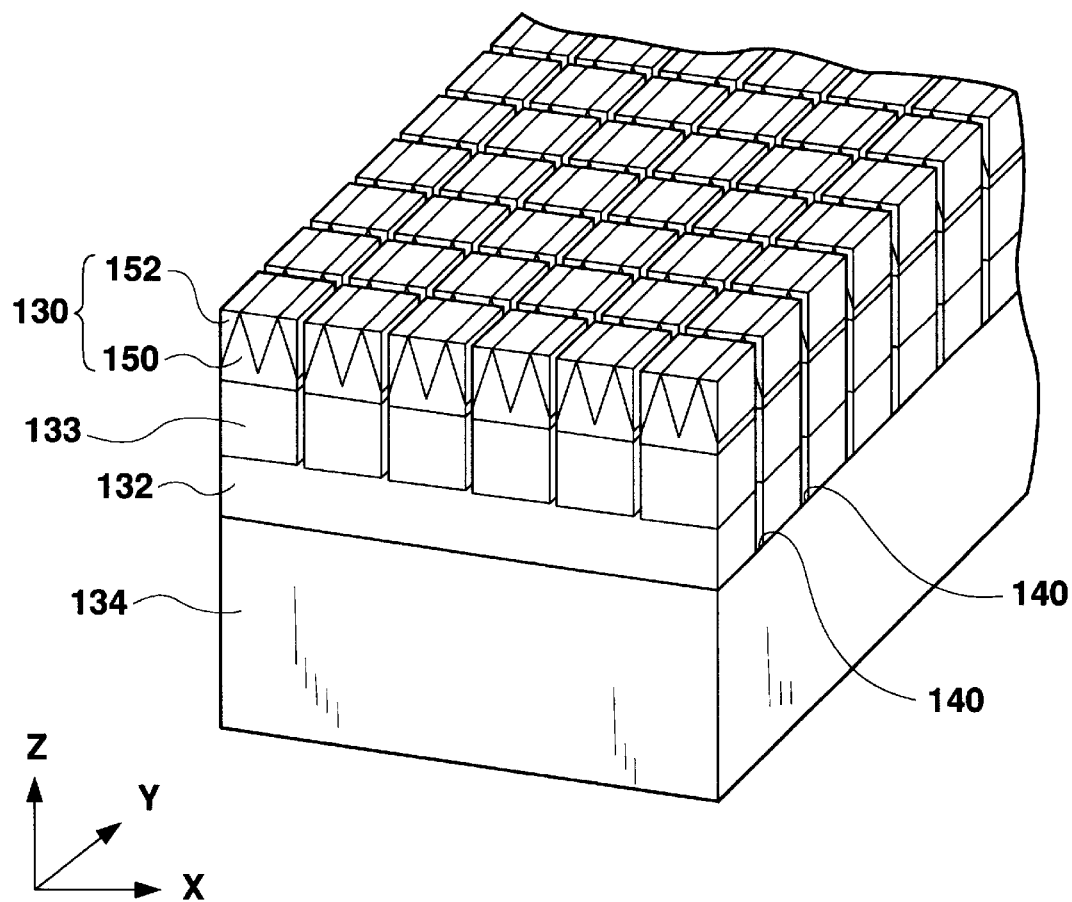
FIG. 11 is a perspective view of the ultrasonic probe shown in FIG. 10.

FIGS. 10 and 11 show another embodiment of an ultrasonic probe.

FIG. 10 is a schematic cross sectional view of an ultrasonic probe and FIG. 11 is a perspective view of the ultrasonic probe. In these drawings, signal leads 14, ground leads 16, sonic speed control leads 20, etc. are not shown.

The ultrasonic probe comprises a plurality of acoustic matching layers 130 which are two-dimensionally arranged, a plurality of sonic speed control elements 133 which are two-dimensionally arranged, a plurality of transducer elements 132 which are one-dimensionally arranged, and a backing layer 134. Each of the members is layered in the Z direction. Each of the transducer elements 132 comprises a piezoelectric plate and electrode layers formed respectively on the upper surface and the lower surface of the piezoelectric plate. The backing layer 134 is for absorbing unnecessary ultrasonic waves radiated from the transducer elements 132 towards the back surface. Each of the acoustic matching layers 130 is respectively provided between the living body and each of the sonic speed control elements 133, to acoustically match the living body and the sonic speed control elements 133.

Each of the sonic speed control elements 133 has a function to adjust the sonic speed of the ultrasonic waves traveling therethrough. Each of the sonic speed control elements 133 may have either the inclined characteristic in the specific acoustic impedance as described above or a uniform characteristic (non-inclined characteristic) in the specific acoustic impedance.

As shown in FIG. 11, the plurality of transducer elements 132 is aligned in the Y direction. In other words, the plurality of transducer elements 132 constitutes a 1-D array transducer. For each transducer element 132, a plurality of sonic speed control elements 133 is provided which are aligned along the X direction. The structure shown in FIG. 11 is similar to the structure shown in FIG. 4.

For the plurality of transducer elements 132, a cut-in channel 140 is formed between adjacent transducer elements 132. These cut-in channels 140 extend in the X direction and are formed using a dicing saw or the like. Similarly, a cut-in channel is formed between the adjacent sonic speed control elements 133 and between adjacent acoustic matching layers 130 using a dicing saw or the like. The se cut-in channels extend in the X direction and in the Y direction.

In the embodiment, the acoustic matching layer 130 comprises a first member 150 and a second member 152 which have differing specific acoustic impedances and overlap in the Z direction. The first member 150 is constructed from a material having a specific acoustic impedance $Z_1$ which is similar to that of the sonic speed control element 133. The first member 150 comprises a plurality of first elements 154 having a pinnacle shape with the top edge directed toward the living body (Z direction). One or a plurality of first elements 154 is formed for each of the acoustic matching layers 130, the number of which is determined by conditions that will be described below. In general, a plurality of first elements 154 is formed for each of the acoustic matching layers 130. The plurality of first elements 154 is connected to each other at their lower sections. On the other hand, a second member 152 is constructed from a material having a specific acoustic impedance $Z_2$ similar to the living body. The second member comprises a second element 155 having a shape that fits the gaps formed between the plurality of first elements 154 and at both ends of the first member 150. In any case, the first member 150 comprises at least one first element 154 which projects toward the living body (upper side) and the second member 152 comprises at least one second element 155 which projects away from the living body (lower side). Because the upper surface of the first member 150 and the lower surface of the second member 152 are completely contacted with each other, there is no layer of air at the boundary surface. With the alternate arrangement of the plurality of first elements 154 and the plurality of second elements 155, the specific acoustic impedance within the acoustic matching layer 130 is continuously varied along the direction of travel of the ultrasonic waves (Z direction). In other words, the acoustic matching layer 130 has an inclined characteristic in the specific acoustic impedance.

Figure 12:
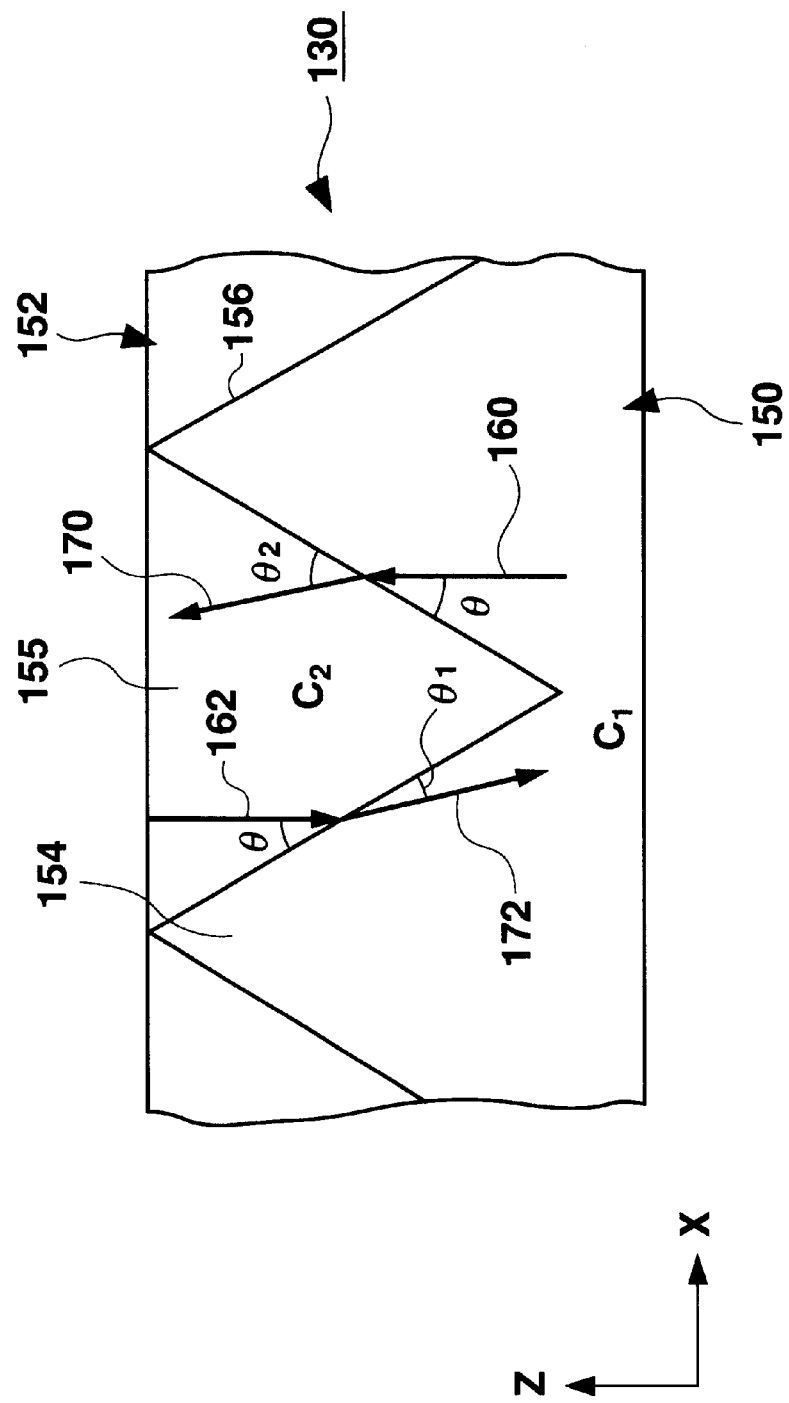
FIG. 12 is a schematic view showing the function of the acoustic matching layer shown in FIG. 10.

FIG. 12 is an enlarging schematic view of the acoustic matching layer 130 shown in FIG. 10. The first element 154 has a "Λ" shape (wedge shape) in which the vertical cross section seen from the Y direction (refer to FIG. 11) is an isosceles triangle. The vertical cross section of the first element 154 seen from the X direction has a rectangular shape. The vertical cross section of the second element 155 seen from the Y direction (refer to FIG. 11) is an isosceles triangle. The vertical cross section of the second element 155 seen from the X direction is a rectangle. The shapes of the elements 154 and 155, however, are not limited to the ones shown in these figures.

The boundary 156 between the first member 150 and the second member 152 is formed as two types of alternately connected surface elements having different orientation. The angle between each of the surface elements and the normal with respect to the surface of the acoustic matching layer 130 (Z direction) is θ. The angle θ is determined by conditions which will be described later.

The transmitted ultrasonic waves propagating from the transducer element via the sonic speed control element primarily propagate in the direction of the normal. In FIG. 12, an arrow 160 represents the direction of the transmitted ultrasonic waves. The transmitted ultrasonic waves propagate in the first member 150 in the direction of the normal. The received ultrasonic waves coming from the living body are primarily incident perpendicular to the surface of the acoustic matching layer 130 and propagates in the direction of the normal. In FIG. 12, an arrow 162 represents the direction of the received ultrasonic waves in the second member 152.

Here, the sonic speed of the ultrasonic waves within the first member 150 is defined as $C_1$. Similarly, the sonic speed of the ultrasonic waves within the second member 152 is defined as $C_2$. When the sonic speed $C_1$ is equal to the sonic speed $C_2$ ($C_1=C_2$), total internal reflection is not generated at the boundary 156 for either the transmitted ultrasonic waves or the received ultrasonic waves. However, in general, because the first member 150 and the second member 152 are formed from different materials, there is some difference in the sonic speeds $C_1$ and $C_2$.

The behaviors of the transmitted ultrasonic waves and of the received ultrasonic waves within the acoustic matching layer 130 will now be described for a case where $C_1>C_2$. For the case where $C_1<C_2$, the behaviors of the transmitted ultrasonic waves and of the received ultrasonic waves will merely be inverted compared to the case of $C_1>C_2$, and thus, will not described.

The behavior of the transmitted ultrasonic waves within the acoustic matching layer 130 is first described. In the acoustic matching layer 130, the transmitted ultrasonic waves 160 incident perpendicularly from the surface near the sonic speed control element 133 is incident on the boundary 156 with an angle θ, and is refracted in the direction of an arrow 170. The angle $\theta_2$ between the arrow 170 and the boundary 156 can be obtained from Snell's law as follows.

$$\cos\theta_2/\cos\theta = C_2/C_1 \quad \text{(Equation 3)}$$

Because the transmitted ultrasonic waves is incident from the first member 150 having a larger sonic speed $C_1$ to the second member 152 having a smaller sonic speed $C_2$, no total internal reflection is generated at the boundary 156.

Next, the behaviors of the received ultrasonic waves in the acoustic matching layer 130 will be described. In the acoustic matching layer 130, the received ultrasonic waves incident perpendicularly from the surface near the living body (arrow 162) is incident on the boundary with an angle θ, and is refracted in the direction of an arrow 172. The angle $\theta_1$ between the arrow 172 and the boundary 156 can be obtained from Snell's law as follows.

$$\cos\theta_1/\cos\theta = C_1/C_2 \quad \text{(Equation 4)}$$

The slope angle θ of the boundary 156 is set to satisfy the following equation.

$$C_1 \geq C_2/\cos\theta \quad \text{(Equation 5)}$$

When the slope angle θ of the boundary 156 is set so that it satisfies the above equation, a relationship, $\theta_1>0$, can be deduced from equation (4), which means that no total internal reflection is generated at the boundary for the received ultrasonic waves that is incident vertically on the acoustic matching layer 130.

The above equation (5) sets the lower limit for θ. The lower limit is determined by the ratio between $C_1$ and $C_2$. That is, as the value of $C_2/C_1$ approaches 1, the lower limit of θ approaches 0.

When θ is determined in reality, a few other points must be considered. In order to form a plurality of first elements having a pinnacle shape to realize quasi-inclination of the specific acoustic impedance, a condition, θ>90°, must be satisfied, because when θ=90°, the boundary 156 becomes flat. As θ becomes larger, the arrangement pitch of the plurality of first elements 154 becomes larger, resulting in reduction in the effect of the quasi-inclination of the specific acoustic impedance. Therefore, in order to desirably realize the inclination of the specific acoustic impedance by the plurality of first elements 154, the arrangement pitch for the plurality of the first elements 154 is preferably as small as possible. For example, it is preferable to set the arrangement pitch for the plurality of first elements 154 to be less than or equal to ½ of the wavelength of the ultrasonic waves. It is also preferable to set the height of each of the first elements 154 to greater than or equal to ½ of the wavelength of the ultrasonic waves. Considering these points, it is preferable that 74 is as small as possible.

On the other hand, received ultrasonic waves may be incident from a direction tilted from the normal with respect to the surface of the acoustic matching layer 130 (here, the incident angle of the ultrasonic waves with respect to the normal is defined as Δθ). In order to produce no total internal reflection at the boundary 156 and allow the received ultrasonic waves incident at a tilted angle to reach the sonic speed control element 133, the lower limit of θ must be a value shifted up from the value defined by the equation (5). The increase in the lower limit of θ depends on the maximum value of Δθ at which the received ultrasonic waves can be received. As the maximum value of Δθ increases, the lower limit of θ also increases. Furthermore, in general, as the angle of the top edge of the first element 154 and of the second element 155 becomes more acute, the machining becomes more difficult. This machining constraint also sets a lower limit for θ. As described, for decreasing θ, there are a number of other constraints in addition to the condition set forth by the above equation (5).

It is preferable that the angle of slope θ be determined considering these various conditions.

The first member 150 is constructed by, for example, adding an additive material (filler) onto a base material. The base material is, for example, an epoxy resin. The filler is, for example, tungsten, tungsten carborundum, tungsten silicide, tantalum, or the like. The epoxy resin is a material having itself a low specific acoustic impedance of about 3 MRayl. A filler having a high specific acoustic impedance is added to the base material. In this manner, a specific acoustic impedance value which is similar to that of the piezoelectric material can be obtained. For example, a first member made by adding a large amount of tungsten powder to an epoxy resin has a specific acoustic impedance of 20 MRayl and a sonic speed $C_1$ of 1600 m/sec.

The second member 152 is constructed from, for example, a poly-ether-block-amido-copolymer, an epoxy resin to which silicone powder is added, a silicone rubber, a butadiene rubber, or the like. By using these materials, the specific acoustic impedance $Z_2$ of the second member 152 can be set to be about 1.6 MRayl which is very close to the specific acoustic impedance of the living body surface. Also, the above materials allow the sonic speed $C_2$ of the second member 152 to be approximately 1600 m/s which corresponds to the sonic speed $C_1$ of the first member 150.

Figure 13:
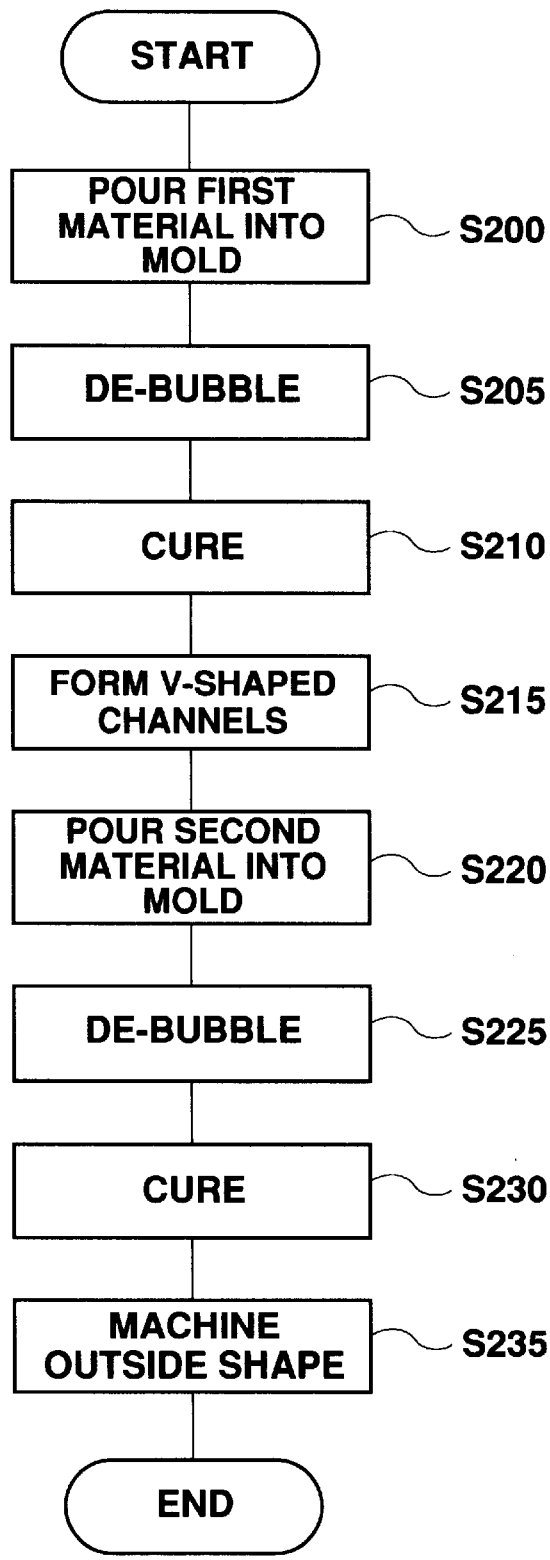
FIG. 13 is a flowchart showing an example method for manufacturing the acoustic matching layer shown in FIG. 10.

FIG. 13 is a flowchart for explaining the manufacturing steps of the acoustic matching layer 130. First, a base plate is formed as the original material for creating a first member 150. More specifically, a mixture solution (first material) in which a filler such as tungsten-carborundum powder is mixed to a liquid-phase epoxy resin is used, and the mixture solution is poured into a mold(step S200). Within the mixture solution, air is present which is mixed during the addition of filler. To this end, the mixture solution poured into the mold is left under a normal temperature for de-bubbling, that is, to remove air (step S205). In order to promote de-bubbling, it is preferable to store the mixture solution inside a depressurized container. After de-bubbling, the mixture solution is cured. More specifically, because an epoxy resin is a thermosetting resin, the mixture solution is introduced into a thermostat, and cured under a normal pressure, a normal humidity, and a high temperature such as, for example, 100° C., for 5 hours (step S210). Through this curing process, the base plate is completed.

A plurality of channels having a V-shape is then formed on the cured base plate. In this manner, a plurality of first elements 154 are formed. In this case, a dicing saw is placed tilted with respect to the base plate material and cutting is performed by the dicing saw along one tilted surface of the first element 154 having a Λ shape. Then, the slope of the dicing saw is changed and cutting is performed along the other tilted surface of the first element 154 (step S215). In this manner, a base plate (machined base plate) onto which a plurality of first elements are formed is completed. The machined base plate has a shape in which a plurality of first members are interconnected.

Next, the machined base plate is again surrounded by a mold. A liquid material (second material) for constituting the second member 152 is poured into the mold (step S220). Then, similar to step S205, a de-bubbling process is applied (step S225), in order to ensure that the poured material fills to the corners of the V-shaped channels between the plurality of first elements 154 and to remove the mixed air bubbles. After de-bubbling process, the liquid material is cured similar to step S210 (step S230). By the curing process, an acoustic matching plate corresponding to a plurality of linked acoustic matching layers is constructed. A machining process for the external shape is applied to the acoustic matching plate. More specifically, in order to secure flatness and parallelity between upper and lower surfaces of the acoustic matching plate, a grinding process is applied to these surfaces (step S235).

The coupling plate produced as above is abutted to the sonic speed control plate at the assembly step of the ultrasonic probe. For the combined structure of the acoustic matching plate and the sonic speed control plate, a cutting process is applied a plurality of times along the X direction and the Y direction using a dicing saw or the like. In this manner, a plurality of acoustic matching layers 130 and a plurality of sonic speed control elements 133 are separately formed.

In the above description, the acoustic matching layer is formed from two members (that is, a first member and a second member). It is also possible that the acoustic matching layer is formed from a larger number of members. However, it is preferable to construct the acoustic matching layer so that, in a plurality of members, the boundary between the adjacent members has a shape with a plurality of hills and valleys.

Figure 14:
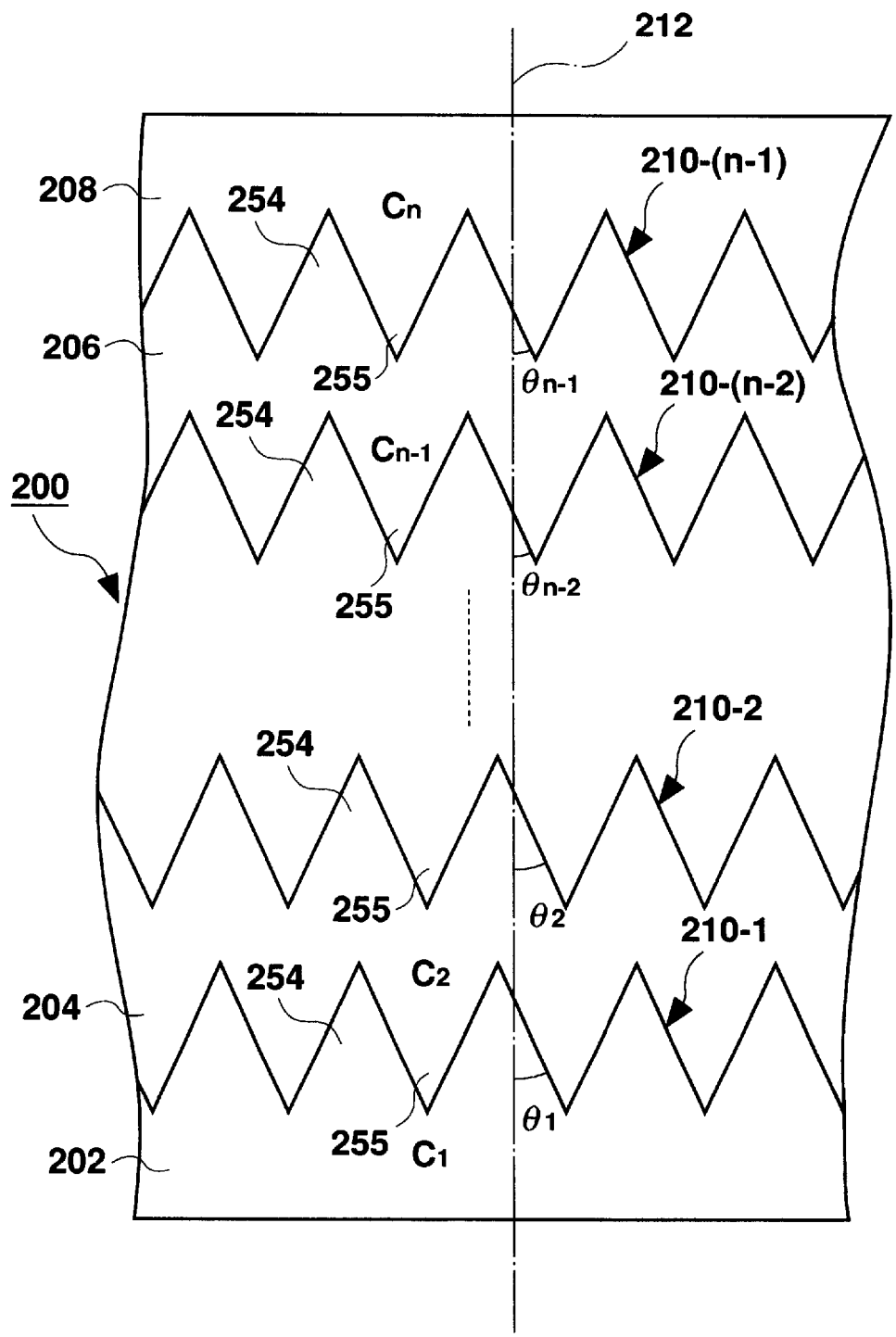
FIG. 14 is a cross sectional view showing an acoustic matching layer comprising a plurality of members (sub-layers).
Figure 15:
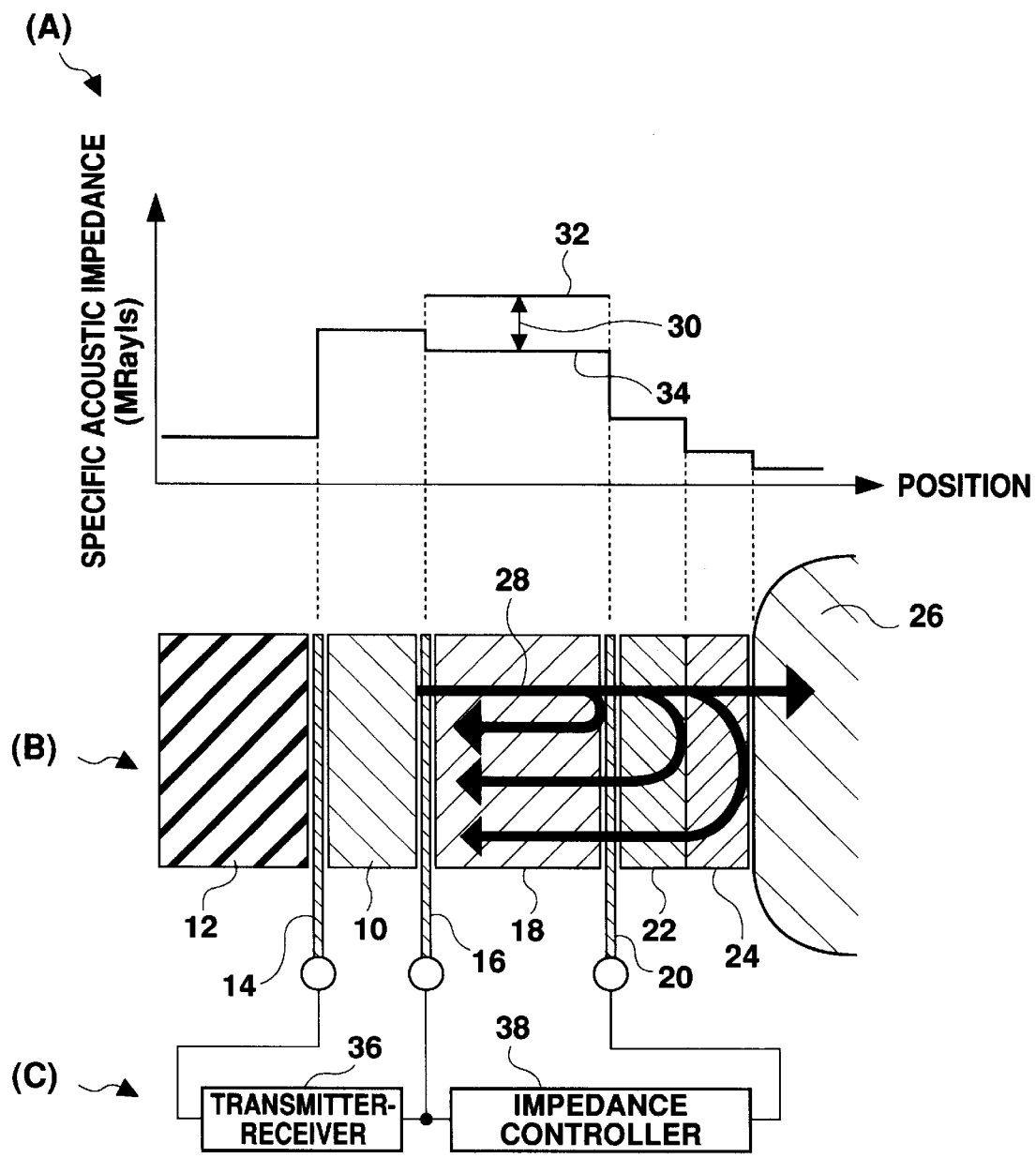
FIG. 15 is a cross sectional view of a conventional ultrasonic probe.

FIG. 14 is a vertical cross sectional view schematically showing an acoustic matching layer 200 made of n members (n≦3). The acoustic matching layer 200 comprises a first member 202, a second member 204, . . . , an (n−1)-th member 206, and an n-th member 208, all of which are layered from the side near the sonic speed control element towards the living body. A plurality of first elements 254 having a pinnacle shape with the top edge (or vertex) pointing towards the living body are formed on (the upper section of) each of the members other than the upper-most, n-th member 208. In contrast, a plurality of second members 255 having a pinnacle shape with the top edge (or vertex) pointing towards the lower side are formed on (the lower section of) each of the members other than the lower-most, first member 202. The plurality of second elements 255 fit with the plurality of first elements 254 in the valley between the plurality of the first elements 254. In other words, between two adjacent members, the lower surface of the upper member and the upper surface of the lower member are completely abutted. The first member 202 is constructed from a material having a specific acoustic impedance $Z_1$ similar to that of the sonic speed control element. The n-th member 208 is constructed from a material having a specific acoustic impedance $Z_n$ similar to that of the living body. The material for each of the members are selected so that the specific acoustic impedance of the members monotonically changes from $Z_1$ to $Z_n$. With the monotonic change in the specific acoustic impedance and the fact that the boundary between two adjacent sub-layers have a shape with hills and valleys, an acoustic matching layer 200 having essentially an inclined characteristic in the specific acoustic impedance can be realized.

The n members are constructed based on conditions similar to the conditions explained referring to FIG. 12. In the following description, the boundary between the k-th member and the (k−1)-th member (here, $1 \leq k \leq (n-1)$) is represented by a reference numeral 210-k. At a boundary 210-k, the conditions related to the slope angle of the boundary 210-k for reducing the generation of total internal reflection of the ultrasonic are:

$$C_{k+1} < C_k < C_{k+1}/\cos \theta_k \qquad \text{(Equation 6)}$$

or $$C_k < C_{k+1} < C_k/\cos \theta_k \qquad \text{(Equation 7)}$$

or $$C_k = C_{k+1} \qquad \text{(Equation 8)}$$

where $C_k$ is the sonic speed of ultrasonic waves in the k-th member ($1 \leq k \leq n$), $\theta_k$ is the angle between the normal 212 with respect to the surface of the acoustic matching layer 200 and the boundary 210-k.

If all of the boundaries 210-k ($1 \leq k \leq (n-1)$) are formed to satisfy the above conditions, propagation of the transmitted ultrasonic waves and the received ultrasonic waves through the acoustic matching layer 200 can be improved.

In the above description, each of the acoustic matching layers 130 and 200 are individually separated. It is also possible to link the acoustic matching layers 130 and 200 in the X direction and/or Y direction. In order to reduce the cross-talk of ultrasonic waves, however, it is preferable that each of the acoustic matching layers 130 and 200 is individually separated.

In the above acoustic matching layers 130 and 200, a plurality of first elements 154 and 254 and a plurality of second elements 155 and 255 are arranged in the elevation direction (X direction) It is also possible to set the plurality of first elements 154 and 254 and the plurality of second elements 155 and 255 to be arranged in the electronic scan direction (arrangement direction of the transducer elements).

The shape of the elements 154 and 254 may be a pyramid. In the above description, the surface elements forming the boundaries 156 and 210-k are tilted planes and the angles of tilt θ and $θ_k$ are constant. However, the angle of tilt θ and $θ_k$ may vary on the boundaries 156 and 210-k as long as the equation (6), (7), or (8) is satisfied at all points on the boundaries 156 and 210-k. In other words, the boundaries 156 and 210-k may be formed from curved surfaces.

What is claimed is:

1. An ultrasonic probe comprising:
   a transducer element for transmitting and receiving ultrasonic waves;
   a sonic speed control element provided at a side of said transducer element near a living body and through which said ultrasonic waves transmitted or received by said transducer element travel, said sonic speed control element having a function to control a sonic speed of said ultrasonic waves traveling therethrough and having an inclined characteristic in the sonic speed control effect in which the sonic speed control effect is gradually changed along a direction of travel of said ultrasonic waves over the whole sonic speed control element or in a portion of said sonic speed control element in said direction of travel; and
   an acoustic matching layer provided at the side of said sonic speed control element near the living body.

2. An ultrasonic probe according to claim 1, wherein a specific acoustic impedance characteristic within said acoustic matching layer is set based on a specific acoustic impedance of said sonic speed control element at the end near a living body and a specific acoustic impedance of said living body.

3. An ultrasonic probe according to claim 1, wherein
   said sonic speed control effect of the sonic speed control element is gradually reduced from a side of said sonic speed control element away from the living body towards an end of the sonic speed control element near the living body; and
   the specific acoustic impedance of said acoustic matching layer corresponds to a specific acoustic impedance of said end of the sonic speed control element near the living body.

4. An ultrasonic probe according to claim 1, wherein
   said sonic speed control element is made of a piezoelectric material; and
   a piezoelectric constant of said piezoelectric material changes along said direction of travel.

5. An ultrasonic probe according to claim 4, wherein said piezoelectric constant gradually decreases from a middle portion of said sonic speed control element towards an end of the sonic speed control element near the living body.

6. An ultrasonic probe according to claim 5, wherein said piezoelectric constant at said end of the sonic speed control element near the living body is zero.

7. An ultrasonic probe according to claim 4, wherein said piezoelectric constant gradually decreases from the middle portion of said sonic speed control element towards said end of the sonic speed control element near the living body and towards said end of the sonic speed control element away from the living body.

8. An ultrasonic probe according to claim 7, wherein said piezoelectric constants at said ends of the sonic speed control element near the living body and away from the living body are zero.

9. An ultrasonic probe according to claim 1, wherein said acoustic matching layer has an inclined characteristic in the specific acoustic impedance in which the specific acoustic impedance gradually changes from the end away from the living body toward the end near the living body.

10. An ultrasonic probe according to claim 9, wherein
    said specific acoustic impedance of the end of said acoustic matching layer away from the living body agrees with the specific acoustic impedance of the end of said sonic speed control element near the living body; and
    the specific acoustic impedance of the end of said acoustic matching layer near said living body agrees with the specific acoustic impedance of said living body.

11. An ultrasonic probe according to claim 10, wherein
    said acoustic matching layer comprises a first member and a second member having different specific acoustic impedances; and
    a compositional ratio between said first member and said second member changes along said direction of travel.

12. An ultrasonic probe according to claim 11, wherein
    said first member has a specific acoustic impedance which is equal to the specific acoustic impedance of said end of the sonic speed control element near the living body; and
    said second member has a specific acoustic impedance which is equal to the specific acoustic impedance of said living body.

13. An ultrasonic probe according to claim 12, wherein
    said first member comprises a plurality of pyramid elements having a pinnacle shape projecting towards the living body; and
    said second member is filled into a gap between said plurality of pyramid elements.

14. An ultrasonic probe comprising:
    N transducer elements for transmitting and receiving ultrasonic waves;
    N×M sonic speed control elements provided at ends of said N transducer elements near a living body and through which said ultrasonic waves travel, with M sonic speed control elements provided for each transducer element, each sonic speed control element having a function to control a sonic speed of the ultrasonic waves traveling therethrough and having an inclined characteristic in the sonic speed control effect in which the sonic speed control effect gradually changes along a direction of travel of the ultrasonic waves over an entire length of, or over a portion of, said direction of travel; and
    N×M acoustic matching layers provided at a side of said N×M sonic speed control elements near the living body.

15. An ultrasonic probe comprising:
    a transducer element for transmitting and receiving ultrasonic waves;
    a sonic speed control element provided at a side of said transducer element near a living body and through which the ultrasonic waves travel, said sonic speed control element having a function to control a sonic speed of the ultrasonic waves traveling therethrough; and
    an acoustic matching layer provided at the side of said sonic speed control element near the living body and having an inclined characteristic in a specific acoustic impedance in which the specific acoustic impedance monotonically changes along a direction of travel of the ultrasonic waves.

16. An ultrasonic probe according to claim 15, wherein said sonic speed control element has a non-inclined characteristic in the sonic speed control effect in which the sonic speed control effect is uniform at every position in said direction of travel.

17. An ultrasonic probe according to claim 15, wherein said sonic speed control element has an inclined characteristic in the sonic speed control effect in which the sonic speed control effect gradually changes along said direction of travel.

18. An ultrasonic probe according to claim 15, wherein
said acoustic matching layer comprises a first member and a second member overlapped in said direction of travel;
said first member and said second member have different specific acoustic impedances; and
a boundary between said first member and said second member has a shape with a plurality of hills and valleys.

19. An ultrasonic probe according to claim 18, wherein when a crossing angle between said direction of travel and said boundary is $\theta$, a sonic speed of said ultrasonic waves within said first member is $C_1$, and a sonic speed of said ultrasonic waves within said second member is $C_2$, a condition, $$C_2 < C_1 < C_2/\cos\theta$$

or a condition, $$C_2 = C_1$$

is satisfied.

20. An ultrasonic probe according to claim 19, wherein
one member, of said first member and said second member, provided near the living body has a specific acoustic impedance corresponding to a specific acoustic impedance of the living body; and
an other member of said first member and said second member provided away from the living body has a specific acoustic impedance corresponding to a specific acoustic impedance of said sonic speed control element.

21. An ultrasonic probe according to claim 20, wherein
one member of said first member and said second member comprises a plurality of first elements having a pinnacle shape; and
the other member of said first member and said second member comprises a plurality of second elements having a shape to fit in a valley section between said plurality of first elements.

22. An ultrasonic probe according to claim 21, wherein said pinnacle shape is a pyramid shape.

23. An ultrasonic probe according to claim 21, wherein a pitch of said plurality of first elements is less than or equal to ½ of a wavelength of said ultrasonic waves.

24. An ultrasonic probe according to claim 21, wherein a depth of said valley section is greater than or equal to ½ of a wavelength of said ultrasonic waves.

25. An ultrasonic probe, comprising:
a transducer element for transmitting and receiving ultrasonic waves;
a sonic speed control element provided at a side of said transducer element near a living body and through which the ultrasonic waves travel, said sonic speed control element having a function to control a sonic speed of the ultrasonic waves traveling therethrough; and
an acoustic matching layer provided at the side of said sonic speed control element near the living body and having an inclined characteristic in a specific acoustic impedance in which the specific acoustic impedance monotonically changes along a direction of travel, the acoustic matching layer made of n members (where n is an integer grater than or equal to 3) overlapped in said direction of travel, and a specific acoustic impedances of said n members changing in steps along said direction of travel.

26. An ultrasonic probe according to claim 25, wherein each of boundaries between said n members has a shape with hills and valleys.

27. An ultrasonic probe according to claim 26, wherein a crossing angle between said direction of travel and the boundary between a k-th member (where k is an integer satisfying the condition, $1 \leq k \leq (n-1)$) and (k+1)-th member is $\theta_k$, a sonic speed of the ultrasonic waves within the k-th member is $C_k$, and a sonic speed of the ultrasonic waves within the (k+1)-th member is $C_{k+1}$, a condition, $$C_{k+1} < C_k < C_{k+1}/\cos\theta_k$$

or a condition, $$C_{k+1} = C_k$$

is satisfied.

28. An ultrasonic probe according to claim 27, wherein
a member, among said n members, that is closest to the living body has a specific acoustic impedance corresponding to a specific acoustic impedance of said living body; and
a member, among said n members, that is closest to said sonic speed control element has a specific acoustic impedance corresponding to the specific acoustic impedance of said sonic speed control element.

29. An ultrasonic probe according to claim 27, wherein
one member of said k-th member and said (k+1)-th member comprises a plurality of first elements having a pinnacle shape; and
an other member of said k-th member and said (k+1)-th member comprises a plurality of second elements having a shape that fits into a valley section between said plurality of first elements having a pinnacle shape.

30. An ultrasonic probe according to claim 29, wherein said pinnacle shape is a pyramid.

31. An ultrasonic probe according to claim 29, wherein a pitch of said plurality of first elements is less than or equal to ½ of a wavelength of said ultrasonic waves.

32. An ultrasonic probe according to claim 26, wherein a depth of the valley section at said plurality of hills and valleys is greater than or equal to ½ of a wavelength of said ultrasonic waves.

* * * * *